US012042213B2

United States Patent
Biber et al.

(10) Patent No.: US 12,042,213 B2
(45) Date of Patent: Jul. 23, 2024

(54) DEVICE FOR CARRYING OUT AN ELECTROSURGICAL INTERVENTION ON A PATIENT

(71) Applicant: Erbe Elektromedizin GmbH, Tuebingen (DE)

(72) Inventors: Ulrich Biber, Reutlingen (DE); Ovidiu Jurjut, Tuebingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 204 days.

(21) Appl. No.: 16/923,791

(22) Filed: Jul. 8, 2020

(65) Prior Publication Data

US 2021/0015547 A1 Jan. 21, 2021

(51) Int. Cl.
*A61B 18/14* (2006.01)
*A61B 17/00* (2006.01)
(Continued)

(52) U.S. Cl.
CPC ...... *A61B 18/1485* (2013.01); *A61B 18/1206* (2013.01); *A61B 2017/00132* (2013.01);
(Continued)

(58) Field of Classification Search
CPC ............ A61B 18/2018; A61B 18/1233; A61B 2018/00577; A61B 2090/061; A61B 5/1106; A61B 2017/00039; A61B 2017/32007; A61B 2018/00595; A61B 2090/064; A61B 5/7207; A61B 10/0275; A61B 10/0283; A61B 17/0218; A61B 17/06109; A61B 17/149; A61B 17/1604;
(Continued)

(56) References Cited

U.S. PATENT DOCUMENTS 4,231,372 A 11/1980 Newton
4,658,815 A * 4/1987 Farin .................. A61B 18/1206
606/34

(Continued)

FOREIGN PATENT DOCUMENTS

DE 32 38 123 A1 4/1984
EP 3505120 A1 7/2019
(Continued)

OTHER PUBLICATIONS

M. Babjuk et al., "EAU Guidelines on Non-Muscle-Invasive Bladder Cancer (Ta, T1 and CIS)." Limited Update Mar. 2016, European Association of Urology, pp. 1-45.
(Continued)

*Primary Examiner* — Linda C Dvorak
*Assistant Examiner* — Abigail Bock
(74) *Attorney, Agent, or Firm* — Blank Rome LLP

(57) ABSTRACT

A surgical device having an apparatus with a generator and an instrument supplied by a generator. A sensor is part of the device that is attached to the patient, for example to an extremity thereof, during surgery to detect the movement of the patient. The sensor is connected with a control device that modifies the operation of generator and particularly switches the generator off, if the sensor detects a movement of the patient exceeding a threshold. Injuries of patient that could occur by involuntary twitches during surgery process are thus avoided.

13 Claims, 3 Drawing Sheets

(51) Int. Cl.
*A61B 18/00* (2006.01)
*A61B 18/12* (2006.01)
*A61B 18/16* (2006.01)

(52) U.S. Cl.
CPC .............. *A61B 2018/00505* (2013.01); *A61B 2018/00601* (2013.01); *A61B 2018/00678* (2013.01); *A61B 2018/00708* (2013.01); *A61B 2018/1253* (2013.01); *A61B 2018/167* (2013.01)

(58) Field of Classification Search
CPC ............ A61B 17/1611; A61B 17/1626; A61B 17/1635; A61B 17/1659; A61B 17/1671; A61B 17/1757; A61B 17/29; A61B 17/320016; A61B 17/32002; A61B 17/32053; A61B 17/3207; A61B 17/320708; A61B 17/320758; A61B 17/320783; A61B 17/3401; A61B 17/3403; A61B 17/3421; A61B 17/3468; A61B 17/3496; A61B 17/683; A61B 17/7065; A61B 17/7068; A61B 17/7092; A61B 17/842; A61B 17/8897; A61B 18/02; A61B 18/14; A61B 18/1477; A61B 18/1487; A61B 18/20; A61B 2017/00261; A61B 2017/00287; A61B 2017/003; A61B 2017/00349; A61B 2017/00469; A61B 2017/00477; A61B 2017/00557; A61B 2017/00867; A61B 2017/00986; A61B 2017/0225; A61B 2017/320004; A61B 2017/320008; A61B 2017/320044; A61B 2017/32006; A61B 2017/320069; A61B 2018/0044; A61B 2018/00565; A61B 2018/00642; A61B 2018/1407; A61B 2018/1412; A61B 2018/1425; A61B 2018/1465; A61B 2034/2048; A61B 2090/0427; A61B 2090/08021; A61B 5/1076; A61B 5/1101; A61B 5/407; A61B 5/721; A61B 90/04; A61B 90/39; A61B 17/07207; A61B 17/320092; A61B 18/1206; A61B 18/1445; A61B 2017/00022; A61B 2017/00026; A61B 2017/00199; A61B 2017/00398; A61B 2017/00734; A61B 2017/07271; A61B 2018/00607; A61B 2018/0063; A61B 2018/00827; A61B 2018/00892; A61B 2018/00988; A61B 2018/00994; A61B 2218/002; A61B 2218/008; A61B 34/30; A61B 17/320068; A61B 18/16; A61B 2017/00075; A61B 2018/00589; A61B 2018/00702; A61B 2018/1253; A61B 2018/1273; A61B 2018/165; A61B 2018/167; A61B 2505/05; A61B 2562/0219; A61B 5/4821; A61B 5/6824; A61B 5/6826; A61B 1/00009; A61B 1/000094; A61B 1/00045; A61B 1/051; A61B 1/0661; A61B 17/0682; A61B 17/072; A61B 17/1114; A61B 17/1155; A61B 17/1285; A61B 18/1442; A61B 2017/0003; A61B 2017/00044; A61B 2017/0057; A61B 2017/00061; A61B 2017/00084; A61B 2017/00097; A61B 2017/00106; A61B 2017/0011; A61B 2017/00115; A61B 2017/00119; A61B 2017/00123; A61B 2017/00203; A61B 2017/00221; A61B 2017/00225; A61B 2017/00402; A61B 2017/00809; A61B 2017/00818; A61B 2017/07257; A61B 2017/07278; A61B 2017/07285; A61B 2017/1132; A61B 2017/320074; A61B 2017/320084; A61B 2017/320095; A61B 2017/320097; A61B 2018/00541; A61B 2018/0066; A61B 2018/00684; A61B 2018/00791; A61B 2018/00839; A61B 2018/00875; A61B 2018/00904; A61B 2018/126; A61B 2018/1266; A61B 2034/2055; A61B 2034/2057; A61B 2034/301; A61B 2034/305; A61B 2090/062; A61B 2090/065; A61B 2090/066; A61B 2090/0807; A61B 2090/0811; A61B 2090/309; A61B 2217/005; A61B 2217/007; A61B 2218/007; A61B 2560/0238; A61B 34/20; A61B 34/25; A61B 34/32; A61B 34/37; A61B 34/71; A61B 5/0066; A61B 5/0075; A61B 5/0261; A61B 5/24; A61B 5/296; A61B 5/395; A61B 5/4519; A61B 5/6833; A61B 5/685; A61B 5/7225; A61B 6/5247; A61B 90/30; A61B 90/35; A61B 90/361; A61B 90/37; A61B 90/90; A61B 1/00006; A61B 1/000096; A61B 1/00103; A61B 1/00105; A61B 1/05; A61B 17/02; A61B 17/2833; A61B 17/285; A61B 18/1402; A61B 18/1485; A61B 2017/00017; A61B 2017/00132; A61B 2017/00154; A61B 2017/00438; A61B 2017/0046; A61B 2017/320094; A61B 2018/00505; A61B 2018/00666; A61B 2018/00678; A61B 2018/00708; A61B 2018/00714; A61B 2018/00732; A61B 2018/00767; A61B 2018/124; A61B 2034/2059; A61B 2090/0808; A61B 5/00; A61B 5/0002; A61B 5/0215; A61B 5/1107; A61B 5/1455; A61B 5/254; A61B 5/4052; A61B 5/411; A61B 5/4836; A61B 5/6825; A61B 5/6828; A61B 5/6829; A61B 5/6831; A61B 5/6832; A61B 5/7275; A61B 5/742; A61B 5/746; A61B 7/003; A61B 17/00

See application file for complete search history.

(56) References Cited

U.S. PATENT DOCUMENTS

| | | | |
|---|---|---|---|
| 8,657,817 B2* | 2/2014 | Fischer | A61B 18/1206 606/42 |
| 9,393,071 B1 | 7/2016 | Boveja et al. | |
| 2012/0316573 A1 | 12/2012 | Durant et al. | |
| 2013/0197503 A1 | 8/2013 | Orszulak | |
| 2014/0303660 A1 | 10/2014 | Boyden et al. | |
| 2015/0282822 A1* | 10/2015 | Trees | A61B 17/282 606/41 |
| 2017/0281054 A1* | 10/2017 | Stever | A61B 5/349 |
| 2020/0188055 A1* | 6/2020 | Bleiler | A61B 90/03 |

FOREIGN PATENT DOCUMENTS

| | | |
|---|---|---|
| JP | 2014523277 A | 9/2014 |
| RU | 2 204 351 C2 | 5/2003 |
| WO | WO 2019/068105 A1 | 4/2019 |

OTHER PUBLICATIONS

The New York School of Regional Anesthesia, ed. Obturator Nerve Block; 2017. Available from: https://www.nysora.com/obturator-nerve-block.

(56) References Cited

OTHER PUBLICATIONS

P.G. Atanassoff et al., "Lidocaine Plasma Levels Following Two Techniques of Obturator Nerve Block." Journal of Clinical Anesthesia, vol. 8, pp. 535-539, 1996.
M. Kakinohana et al., "Interadductor Approach to Obturator Nerve Block for Transurethral Resection Procedure: Comparison with Traditional Approach." Journal of Anesthesia, vol. 16, pp. 123-126, 2002.
C. Deliveliotis et al., "The Contribution of the Obturator Nerve Block in the Transurethral Resection of Bladder Tumors." Acta Urologica Belgica, vol. 63, pp. 51-54, 1995.
R. Schwilick et al., "The Deactivation of the Obturatorius Reflex as Specific Indication for Diluted Etidocaine Solutions. An Examination of the Suitability of the Local Anesthetics for the Reflex Elimination in the Technique of the "3-in-1-block." [original title: Die Ausschaltung des Obturatorius-Reflexes als spezifische Indikation für verdünnte Etidocain-Lösungen. Eine Untersuchung zur Eignung des Lokalanaesthetikums für die Reflex-Elimination in der Technik des „3-in-1 Blocks." Regional Anaesthesie, vol. 13, pp. 6-10, 1990.
J.P. Gasparich et al., "Use of Nerve Stimulator for Simple and Accurate Obturator Nerve Block Before Transurethral Resection." The Journal Urology, vol. 132, pp. 291-293, 1984.
Y. Cui et al., "Comparing the Efficiency and Safety of Bipolar and Monopolar Transurethral Resection for Non-Muscle Invasive Bladder Tumors: A Systematic Review and Meta-Analysis." Journal of Laparoendoscopic & Advanced Surgical Techniques, vol. 26, No. 3, pp. 196-202, 2016.
I.T. Armstrong et al., "Waiting for a Hand: Saccadic Reaction Time Increases in Proportion to Hand Reaction Time when Reaching Under a Visuomotor Reversal." Frontiers in Human Neuroscience, vol. 7, article 319, pp. 1-11, 2013.
F.C. Donders, "On the Speed of Mental Processes." Acta Psychologica, vol. 30, pp. 412-431, 1969.
J. Biserte et al., "Treatment of Superficial Tumors ofthe Bladder with Argon Laser [Original Title: Traitement Des Tumeurs Superficielles De Vessie Par Laser Argon]." Acta Urol. Belg., vol. 57, pp. 697-701, 1989.
M.K. Aas-Eng et al., "Complications in Operative Hysteroscopy—Is Prevention Possible?" Acta Obstet. Gynecol. Scand., vol. 96, pp. 1399-1403, 2017.
M. Alschibaja et al., Recent Improvements in Transurethral High-Frequency Electrosurgery of the Prostate. BJU Int., vol. 97, pp. 243-246, 2006.
P.G. Atanassoff et al., "Electromyographic Comparison of Obturator Nerve Block to Three-In-One Block." Anesth. Analg., vol. 81, pp. 529-533, 1995.
P.G. Atanassoff et al., "Compound Motor Action Potential Recording Distinguishes Differential Onset of Motor Block of the Obturator nerve in Response to Etidocaine or Bupivacaine." Anesth. Analg., vol. 82, pp. 317-320, 1996.
D. Bolat et al., "Impact of Nerve Stimulator-Guided Obturator Nerve Block on the Short-Term Outcomes and Complications of Transurethral Resection of Bladder Tumour: A Prospective Randomized Controlled Study." Can. Urol. Assoc. J., vol. 9, p. E780-4, 2015.
W. Wieland et al., "Transurethral Resection of the Bladder [original title: Transurethrale Resektion der Blase.]" in: Hofman R, ed. Endoscopic Urology [original title: Endoskopische Urologie], Berlin, Heidelberg: Springer Berlin Heidelberg; pp. 151-163, 2009.
C.E. DeSantis et al., "Cancer Treatment and Survivorship Statistics." CA Cancer J. Clin., vol. 64, pp. 252-271, 2014.
J. Ferlay et al., "Estimates of the Cancer Incidence and Mortality in Europe 2006." Ann. Oncol., vol. 18, pp. 581-592, 2007.
N.P. Gupta et al., "Bipolar Energy for Transurethral resection of Bladder Tumours at Low-Power Settings: Initial Experience." BJU Int., vol. 108, pp. 553-556, 2010.
I. Kausch et al., "Recent Improvements in the Detection and Treatment of Nonmuscle-invasive Bladder Cancer." Expert Rev. Anticancer Ther., vol. 6, pp. 1301-1311, 2006.
M. Khorrami et al., "A Comparison Between Blind and Nerve Stimulation Guided Obturator Nerve Block in Transurethral Resection of Bladder Tumor." J. Endourol., vol. 26, pp. 1319-1322, 2012.
F. Mogora et al., "Obturator Nerve Block: An Evaluation of Technique." British Journal of Anaesthesia, vol. 41, pp. 695-698, 1969.
J. Mashni et al., "Prospective Evaluation of Plasma Kinetic Bipolar Resection of Bladder Cancer: Comparison to Monopolar Resection and Pathologic Findings." Int. Urol. Nephrol., vol. 46, pp. 1699-1705, 2014.
K. Ozer et al., "Bladder Injury Secondary to Obturator Reflex is More Common with Plasmakinetic Transurethral Resection than Monopolar Transurethral Resection of Bladder Cancer." Cent. European J. Urol., vol. 68, pp. 284-288, 2015.
H. Shiozawa et al., "A New Transurethral Resection System: Operating in Saline Environment Precludes Obturator Nerve Reflexes." J. Urol., vol. 168, pp. 2665-2667, 2002.
M.S. Shulman et al., "Simultaneous Bilateral Obturator Nerve Stimulation During Transurethral Electrovaporization of the Prostrate." J. Clin. Anesth, vol. 10, pp. 518-521, 1998.
T. Sugihara et al., "Comparison of Perioperative Outcomes Including Sever Bladder Injury Between Monopolar and Bipolar Transurethal Resection of Bladder Tumors: A Population Based Comparison." J. Urol., vol. 192, pp. 1355-1359, 2014.
V. Venkatramani et al., "Monopolar Versus Bipolar Transurethral Resection of Bladder Tumors: A Single Center, Parallel Arm, Randomized, Controlled Trial." J. Urol., vol. 191, pp. 1703-1707.
G. Wendt-Nordahl et al., "The Vista System: A New Bipolar Resection Device for Endourological Procedures: Comparison with Conventional Resectoscope." Eur. Urol., vol. 46, pp. 586-590, 2004.
C. Zhao et al., "Bipolar Versus Monopolar Transurethral Resection of Nonmuscle-Invasive Bladder Cancer: A Meta-Analysis." J. Endourol.., vol. 30, pp. 5-12, 2016.

\* cited by examiner

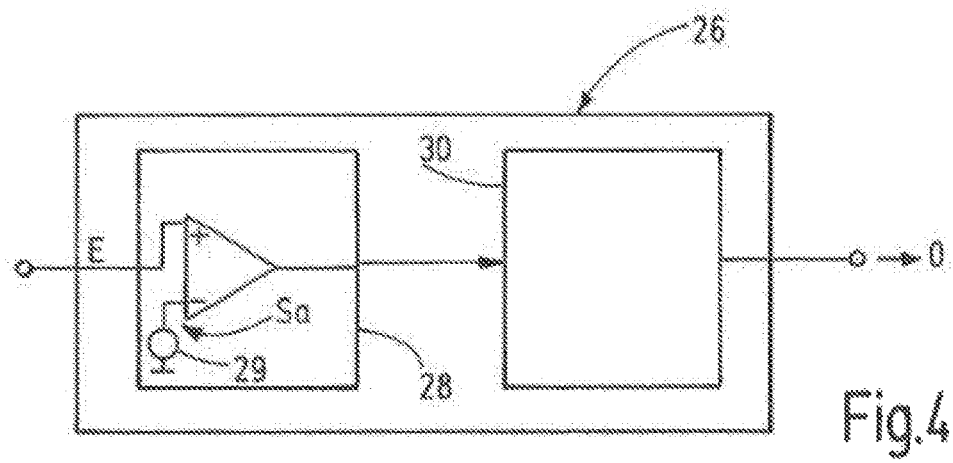
Fig.4
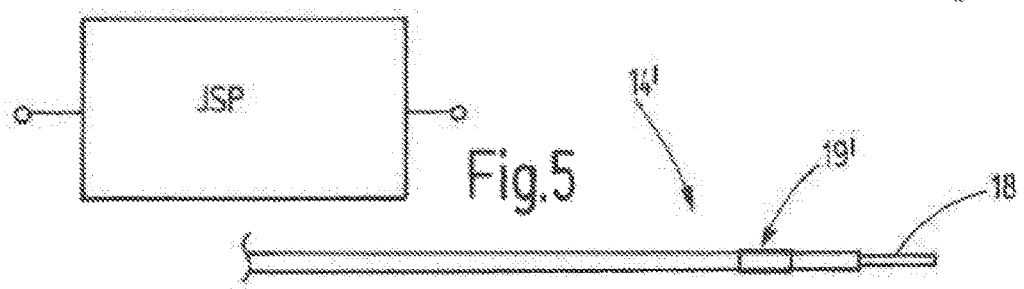
Fig.5
Fig.6
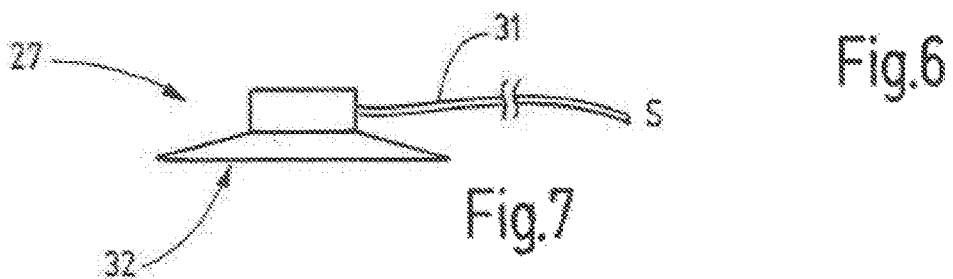
Fig.7
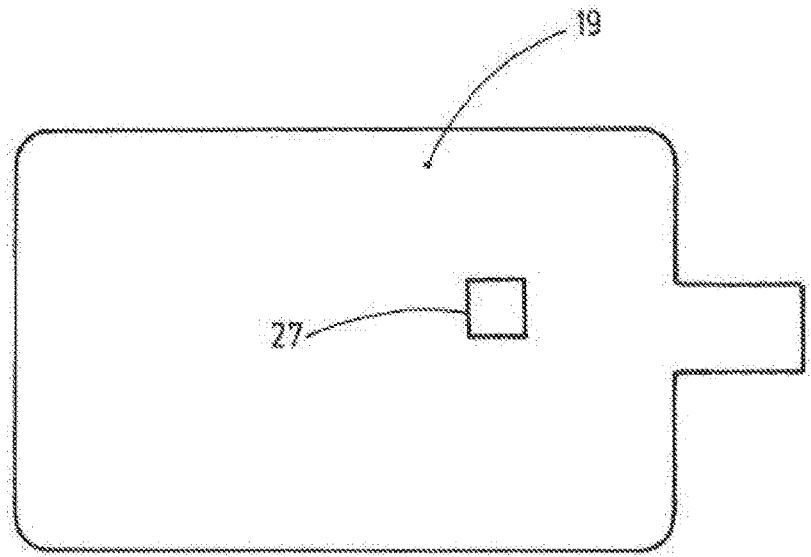
Fig.8

DEVICE FOR CARRYING OUT AN ELECTROSURGICAL INTERVENTION ON A PATIENT

CROSS REFERENCE TO RELATED APPLICATION

This application claims priority to European patent application No. 19187086.4, filed Jul. 18, 2019, the subject matter of which is incorporated by reference herein in its entirety.

TECHNICAL FIELD

A device for carrying out an electrosurgical intervention on a patient, particularly in urology.

BACKGROUND

During surgical interventions, particularly electrosurgical interventions, neuromuscular stimulations can occur in spite of the use of radio frequency current. This also happens, if the frequency of the radio frequency current is over the limit of 100 kHz that is considered as critical limit. Particularly, it refers to the transurethral electro-resection of the bladder, as well as the transurethral electro-resection of the prostate in urology and the hysteroscopic transcervical resection in gynecology. Neuromuscular stimulation in this area can result in a stimulation of the obturator nerve and along therewith a sudden and vehement leg adductor contractions. These contractions can lead to uncontrolled movements on the patient, e.g. instruments introduced in his/her bladder, with the danger of bladder wall perforation. Extensive literature exists with regard to this problem:

1 Ozer K, Horsanali M O, Gorgel S N et al. Bladder injury secondary to obturator reflex is more common with plasmakinetic transurethral resection than monopolar transurethral resection of bladder cancer. Cent European J Urol 2015; 68: 284-288
2 Ferlay J, Autier P, Boniol M et al. Estimates of the cancer incidence and mortality in Europe in 2006. Ann Oncol. 2007; 18: 581-592
3 Kausch I, Doehn C, Jocham D. Recent improvements in the detection and treatment of nonmuscle-invasive bladder cancer. Expert Rev Anticancer Ther 2006; 6: 1301-1311
4 DeSantis C E, Lin C C, Mariotto A B et al. Cancer treatment and survivorship statistics, 2014. CA Cancer J Clin 2014; 64: 252-271
5 Aas-Eng M K, Langebrekke A, Hudelist G. Complications in operative hysteroscopy—is prevention possible? Acta Obstet Gynecol Scand 2017; 96: 1399-1403
6 Shulman M S, Vellayappan U, Monaghan T G et al. Simultaneous bilateral obturator nerve stimulation during transurethral electrovaporization of the prostate. J Clin Anesth 1998; 10: 518-521
7 Magora F, Rozin R, Ben-Menachem Y et al. Obturator nerve block: an evaluation of technique. British Journal of Anaesthesia 1969; 41: 695-698
8 Atanassoff P G, Weiss B M, Brull S J et al. Electromyographic comparison of obturator nerve block to three-in-one block. Anesth Analg 1995; 81: 529-533
9 Atanassoff P G, Weiss B M, Brull S J et al. Compound motor action potential recording distinguishes differential onset of motor block of the obturator nerve in response to etidocaine or bupivacaine, Anesth Analg 1996; 82: 317-320
10 Bolat D, Aydogdu O, Tekgui Z T et al. Impact of nerve stimulator-guided obturator nerve block on the short-term outcomes and complications of transurethral resection of bladder tumour: A prospective randomized controlled study. Can Urol Assoc J 2015; 9: E780-4
11 Khorrami M, Hadi M, Javid A et al. A comparison between blind and nerve stimulation guided obturator nerve block in transurethral resection of bladder tumor. J Endourol 2012; 25: 1319-1322
12 Burger M, Wieland W-F.: "Transurethral resection of the bladder [original title: Transurethrale Resektion der Blase]", in: Hofmann R, ed. Endoscopic urology [original title: Endoskopische Urologie], Berlin, Heidelberg: Springer Berlin Heidelberg; 2009: 151-163
13 Gupta N P, Saini A K, Dogra P N et al. Bipolar energy for transurethral resection of bladder tumours at low-power settings: initial experience. BJU Int 2011; 108: 553-556
14 Biserte J, Brunetaud J M, Rigot J M et al.: "Treatment of superficial tumors of the bladder with argon laser [original title: Traitement des tumeurs superficielles de vessie par laser Argon]", Acta Urol Belg 1989; 57: 697-701
15 Alschibaja M, May F, Treiber U et al. Recent improvements in transurethral high-frequency electrosurgery of the prostate. BJU Int 2006; 97: 243-246
16 Shiozawa H, Aizawa T, Ito T et al. A new transurethral resection system: operating in saline environment precludes obturator nerve reflexes. J Urol 2002; 168: 2665-2667
17 Wendt-Nordahl G, Hacker A, Reich O et al. The Vista system: a new bipolar resection device for endourological procedures: comparison with conventional resectoscope. Eur Urol 2004; 46: 586-590
18 Zhao C, Tang K, Yang H et al. Bipolar Versus Monopolar Transurethral Resection of Nonmuscle-invasive Bladder Cancer: A Meta-Analysis. J Endourol 2016; 30: 5-12
19 Venkatramani V, Panda A, Manojkumar R et al. Monopolar versus bipolar transurethral resection of bladder tumors: a single center, parallel arm, randomized, controlled trial. J Urol 2014; 191: 1703-1707
20 Sugihara T, Yasunaga H, Horiguchi H et al. Comparison of perioperative outcomes including severe bladder injury between monopolar and bipolar transurethral resection of bladder tumors: a population based comparison, J Urol 2014; 192: 1355-1359
21 Mashni J, Godoy G, Haarer C et al. Prospective evaluation of plasma kinetic bipolar resection of bladder cancer: comparison to monopolar resection and pathologic findings. Int Urol Nephrol 2014; 46: 1699-1705
22 Babjuk M, Bohle A, Burger M et al. EAU Guidelines on Non-Muscle-invasive Urothelial Carcinoma of the Bladder: Update 2016. Eur Urol 2017; 71: 447-461
23 The New York School of Regional Anesthesia, ed. Obturator Nerve Block; 2018. Available from: https://www.nysora.com/obturator-nerve-block
24 Atanassoff P G, Weiss B M, Brull S J. Lidocaine plasma levels following two techniques of obturator nerve block, J Clin Anesth 1996; 8: 535-539
25 Kakinohana M, Taira V, Saitoh T et al. Interadductor approach to obturator nerve block for transurethral resection procedure: Comparison with traditional approach. J Anesth 2002; 16: 123-126
26 Deliveliotis C, Alexopoulou K, Picramenos D et al. The contribution of the obturator nerve block in the transurethral resection of bladder tumors. Acta Urol Belg 1995; 63: 51-54
27 Schwilick R, Weingärtner K, Kissler G V et al. The deactivation of the obturatorius reflex as specific indication for deluted etidocaine solutions. An examination of the suitability of the local anesthetics for the reflex elimination in the technique of the "3-in-1-block". [original title: Die Ausschaltung des Obturatorius-Reflexes als spezifische Indikation für verdünnte Etidocain-Lösungen. Eine Untersuchung zur Eignung des Lokatanaesthetikums für die Reflex-Elimination in der Technik des "3-in-1 blocks".] Reg Anaesth 1990; 13:6-10

28 Gasparich J P, Mason J T, Berger R E. Use of nerve stimulator for simple and accurate obturator block before transurethral resection. J Urol 1984; 132: 291-293

29 Cui Y, Chen H, Liu L et al. Comparing the Efficiency and Safety of Bipolar and Monopolar Transurethral Resection for Non-Muscle Invasive Bladder Tumors: A Systematic Review and Meta-Analysis. J Laparoendosc Adv Surg Tech A 2016; 26: 196-202

30 Armstrong I T, Judson M, Munoz D P et al. Waiting for a hand: Saccadic reaction time increases in proportion to hand reaction time when reaching under a visuomotor reversal. Front Hum Neurosci 2013; 7: 319

31 Donders F C. On the speed of mental processes. Acta Psychologica 1969; 30: 412-431

SUMMARY

It is an object of embodiments of the invention to provide a device with which electrosurgical interventions on a patient can be carried out with a reduced surgery risk.

This object is solved with a device according to claim 1:

Embodiments of the inventive surgical device is particularly suitable for carrying out an electrosurgical intervention on a patient, e.g. for carrying out a transurethral electro-resection of the bladder, a transurethral electro-resection of the prostate or the transcervical resection (TURB, TURP, TCR). An apparatus with a generator for creation of treatment voltage with which an instrument is supplied, forms part of the device. In addition, a control device for control of the generator is part of the apparatus. The control of the generator comprises at least switching the generator on and off. In addition, the control of the generator can also comprise the setting of a surgery mode like dissection, ablation, coagulation, etc. Different surgery modes are achieved by adjusting different generator voltages and/or different voltage modulations at the generator. The voltage modulation can be, for example, a pulse width modulation, a frequency modulation or the like.

A sensor configured to be attached to the patient and configured to detect a movement of the patient is also part of the device. The sensor is connected with the control device. In doing so, muscle contractions caused by neuromuscular stimulation can be quickly recognized and used for implementation of a control signal. For example in doing so, the generator can be switched off or can be otherwise influenced in its operation, if an undesired movement of the patient is determined. For example, the control device can be configured to reduce the power of the generator and/or to vary the modulation of the radio frequency voltage and/or to switch off the generator at least during time phases or permanently in case of determination of an undesired movement of the patient.

If the generator is quickly switched off in case of determination of an undesired movement of the patient, the neuromuscular stimulations can be quickly eliminated and the muscle contraction can thus be limited to a non-disturbing, particularly non-dangerous amount. Bladder wall perforations, due to muscle contractions, or other surgical complications are thus avoided.

Preferably the sensor is a position sensor, a movement sensor or an acceleration sensor. The signal output by the sensor configured as position sensor can be timely differentiated (differentiated by the time) one or multiple times, in order to create a signal that indicates sudden movements. In doing so, undesired switch-off due to slow or slight movements of the patient that are harmless for the surgery result, are avoided. Sudden twitches or vehement movements are, however, already detected at the beginning. The sensor creates respective signals that are evaluated by the signal evaluation circuit and are considered for switch-off of the generator.

Advantageously the sensor comprises an attachment device with which it can be attached at an extremity, particularly a foot or a leg of the patient, e.g. at his/her calf. A band encircling the extremity of the patient at a suitable location or also a adhesive area provided at the sensor with which the sensor can be adhesively attached at the skin of the patient is suitable as attachment device.

Advantageously the control device comprises a signal evaluation device that is configured to compare the signal provided by the sensor or a signal derived therefrom with a threshold by a signal processing device and to create a switch-off signal, if the threshold is exceeded.

The signal processing device can comprise one or multiple filters (high pass, low pass, band pass), linear or non-linear amplifiers or the like.

In addition to detecting the threshold exceedance, the signal evaluation device can be configured to output a warning signal before this threshold is reached. For example, a first threshold can be set to an acceleration of about 3 m/s$^2$, whereas the second threshold that shall lead to switch-off, i.e. to safety switch-off, can be an acceleration of e.g. 11 m/s$^2$.

The control device can be configured to block the generator after creation of the switch-off signal and to request a manual release. Alternatively, it can be configured to create the switch-off signal for a defined time duration of, e.g. 3 seconds. Within this time duration the operator can decide how he/she would like to proceed.

It is further possible to provide the control device with an adjustment device, with which the time duration for the switch-off can be adjusted. It is further possible that the control device is provided with input devices for the adjustment of the first and/or second threshold. In addition, the control device can comprise a control for deactivation of the part of the control device that monitors the signal coming from the sensor.

Preferably, the output of a switch-off signal is carried out without delay and thus preferably within less than 30 ms, preferably less than 20 ms after start of a detectable motoric activity of the extremity provided with the sensor. In this short time duration the movements of the extremities initiated due to the muscle contraction, are still very small such that the manual activity of the surgeon is not substantially disturbed, also in case of difficult surgeries.

Embodiments of the inventive device can be used for bipolar instruments that comprise two electrodes, as well as for monopolar instruments that do not have a counter or neutral electrode themselves and for which a neutral electrode has to be attached on the patient.

It is possible to attach the sensor for detection of a movement, particularly an acceleration of an extremity of the patient at or in the neutral electrode that is to be arranged, for example, at the calf of the patient.

Embodiments of the invention can be realized with an apparatus described herein, as well as with apparatus, the internal control device of which is not configured for evaluation of sensor signals. In such apparatus a section forming part of the control device can be arranged external of the apparatus. Such a section connected with the sensor can be, for example, in an activation switch, e.g. a foot switch, or in a separate housing that is connected between the activation conductor coming from the instrument or a foot switch and the activation input of the apparatus.

BRIEF DESCRIPTION OF THE DRAWINGS

Further details of advantageous embodiments of the invention are subject to the claims as well as the drawings and the respective description. The drawings show:

DETAILED DESCRIPTION

Figure 1:
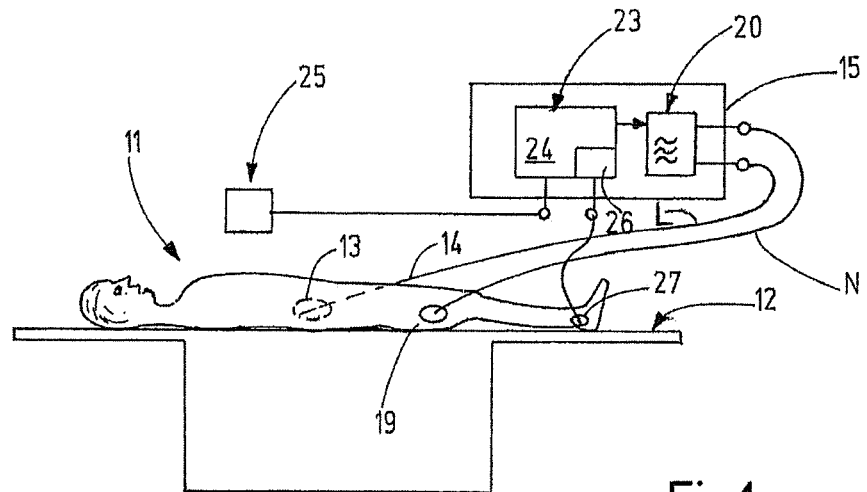
FIG. 1 an embodiment of the inventive device in application on a patient in a schematic illustration, FIG. 2 an instrument for application on a patient in schematic partial view, FIG. 3 the apparatus for supply of the instrument in a schematic block diagram, FIG. 4 a signal evaluation circuit of the apparatus according to FIG. 3 as block diagram, FIG. 5 a signal processing device in a schematic manner, FIG. 6 a modified instrument for treatment of a patient according to FIG. 1, FIG. 7 a sensor for attachment on a patient according to FIG. 1 in a side view, FIG. 8 a neutral electrode with a sensor in a schematic top view, FIG. 9 the function of the signal evaluation device in form of a diagram and FIG. 10 a modified embodiment of the device in a sectional illustration.

FIG. 1 illustrates a surgery situation, in which a patient 11 is supported on a table 12 for carrying out of a surgical intervention that is to be carried out, for example, in a body cavity 13 of the patient, e.g. in the urogenital tract. For this an instrument 14 is inserted into the patient 11 that is connected with a supplying apparatus 15. The instrument 14 is, for example, a probe 16 having a rigid or flexible shaft 17 and an electrode 18 at the end thereof. It can be a monopolar instrument as illustrated. In this case a neutral electrode 19 is attached to the patient 11 that can be formed, for example, by a current diverting electrically conductive adhesive plaster.

The apparatus 15 comprises a generator 20 that is suitable for output of a suitable radio frequency voltage for carrying out a surgical intervention. It is typically in the range of above 100 V, preferably above 200 V with a frequency over, preferably remarkably over 100 kHz. The radio frequency voltage can be non-modulated or modulated, e.g. pulse width modulated. The electrode 18 of the instrument 14 is connected with an output of the generator 20 via an electric conductor L, as illustrated in FIG. 1. The neutral electrode 19 is connected with the other output of the generator 15 via a conductor M.

Figure 3:
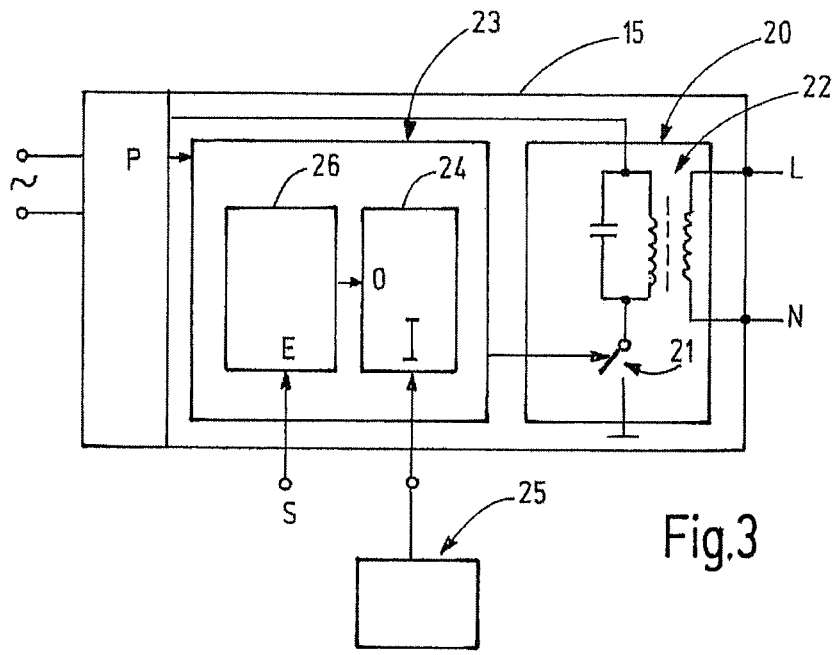

As illustrated in FIG. 3, the generator 20 can consist of a radio frequency power oscillator, the switching element 21 of which stimulates an oscillating circuit 22 from which the supply voltage for the instrument 14 is coupled out in a transformatoric or another manner. A control device 23 that acts, for example, on the switching element 21 in order to excite the oscillating circuit 22 permanently or in a pulse-like manner, serves to control the generator 20. A power supply or another power source P for supply of the control device 23 and the generator 20 is part of the apparatus 15.

The control device 23 is at least configured to activate and deactivate the generator 20. In the active phase the switching element 21 is continuously opened and closed, whereas it remains open (non-conductive) during the deactivated phase.

The control device 23 comprises an activation block 24 having an activation input I that is connected with an activation switch 25. This activation switch 25 can be actuated preferably manually and can be, for example, configured as foot switch or as switch at the instrument 14. The activation block 24 further comprises an inhibiting input 0 that is connected with a deactivation block 26. The deactivation block 26 comprises an input E to which a sensor 27 is connected.

The sensor 27 can be configured as position sensor or as it is preferred, particularly as acceleration sensor. The sensor 27 is suitable to transform its movement into an electrical signal. Particularly, sensor 27 is suitable to output a signal corresponding to the movement speed or acceleration.

The deactivation block 26 is individually illustrated in FIG. 4. It can comprise, for example, a comparator 28 that compares the signal coming from sensor 27 with a threshold (sa) that can be provided, for example, by a threshold provider 29. The signal provided at the output of the comparator 28 characterizes cases in which the signal output from the sensor 27 is larger than the threshold (sa). The output signal of comparator 28 can be supplied, for example, to a block 30 for further processing. This block 30 can fulfill additional functions as desired. Such functions can be: Creation of an inhibiting signal for a predefined or for an adjustable time duration, permanent creation of a switch-off signal until a reset or the like. For example, a reset signal can be provided by the activation switch 25 or an individual reset switch.

As an option, a signal processing device, e.g. in form of a digital signal processor DSP, can be arranged between the sensor 27 and the input E of the deactivation block. It can be programmed to filter or otherwise process the signal output from the sensor 27. Such signal processing can comprise filter blocks, amplifier blocks, pattern recognition blocks or the like. Filter blocks can be low passes, high passes or band passes. Amplifier blocks can be linear or non-linear amplifier blocks.

The device described so far operates as follows:

It is assumed that a surgeon that is not illustrated in FIG. 1, has, as illustrated, inserted the instrument 14 in patient 11 and activated the instrument 14 by activation switch 25. First the deactivation block 26 is inactive, such that the control device 23 allows operation of generator 20. The generator 20 outputs a radio frequency voltage to the instrument 14, particularly at its electrode 18 with which the tissue of patient 11 is effected. The neutral electrode 19 receives the current flowing into the patient and conducts it back to the generator 20.

If the current originating from electrode 18 enters into a nerve path that could cause a remarkable movement of patient 11, particularly in the proximity of the obturator nerve, a sudden leg adductor contraction can occur. Immediately with the beginning of such a movement the sensor 27 detects the movement, particularly the velocity or the acceleration of the movement. If the signal output from the sensor 27 exceeds the threshold (sa) defined by the threshold provider 29, a switch-off signal is generated.

If it is, for example, configured as mono-flop, the processing block 30 can then create a switch-off signal for a fixed or pre-definable time duration, e.g. for 3 s, that is supplied to the input 0 of the activation block 24. The activation block 24 thus switches off the activation of generator 20. The generator 20 is switched off and it does not output a voltage anymore during an inhibiting time period that is defined by processing block 30. In doing so, further stimulation of the nerves and thus a more intense leg movement is efficiently inhibited. Indeed, the treatment process is interrupted at this point of time at least shortly, however, substantial risks of injury due to sudden leg movements of the patient 11 are avoided. In doing so, also surgery complications are effectively avoided that could otherwise occur.

Numerous modifications of embodiments of the invention described so far are possible. A first supplement that is possible in all of the embodiments described above or below is the use of multiple sensors 27 that can be attached to different locations of an extremity or to different extremities, particularly both legs of patient 11. In this case signals of the two or more sensor can be summed and provided to the input E of the comparator 28. Also an individual comparator with an individual input can be provided for each sensor, wherein the output signals of these comparators can be logically combined such that switch-off occurs if at least one of the comparators provides a switch-off signal (OR-connection).

It is further possible to arrange the deactivation block 26 external of the apparatus 15. In this case the deactivation block 26 external of the apparatus 15 is still considered as part of the control device of the apparatus 15 and, for example, arranged in the activation switch 25. The deactivation block 26 can be configured according to any of the embodiments described above in this case and can be configured for monitoring of one or more sensors. In case of a deactivation, it can for example interrupt or short-circuit the signal provided by the activation switch 24 to the input I of the control device 23.

The deactivation block can also be arranged in instrument 14, particularly if the activation switch 25 is arranged at the instrument. In doing so, it is advantageous, if sensor 27 is connected via a wireless connection with the deactivation block.

In a further modified embodiment the deactivation block can be connected to the generator output of the generator 20, e.g. in order to short-circuit the voltage provided there in case of a deactivation event. Alternatively, the deactivation block 26 can be integrated into the instrument 14.

The center 27 is individually schematically illustrated in FIG. 7. It can be configured as wireless sensor and can transmit the signal created by itself, e.g. the signal characterizing the movement speed or the acceleration, in a wireless manner to the deactivation block 26. Alternatively, sensor 27 can be provided with a cable 31 that is to be connected at the connection E of the deactivation block 26.

The sensor 27 can be provided with an adhesive area 32 for attachment on the patient, the adhesive area 32 being coated with glue or adhesive in order to allow attachment on the skin of a patient. Alternatively, an attachment strap can be attached to the sensor 27 with which the sensor can be strapped to the patient.

It is further possible to monitor the signal provided by sensor 27 from time to time or continuously for validity, e.g. in order to timely identify a sensor 27 that is not correctly attached on the patient or has fallen off the patient. For this each of the described embodiments can be supplemented with a monitoring block that is connected with a signal output from the sensor. The monitoring block can be configured to classify the signal provided by sensor 27 as valid signal only in the case, if it exceeds the background noise of the sensor 27 and thus indicates omnipresent micro-movements of the patient 11. If such signals are no longer received, the deactivation block 26 may signal the invalidity of the sensor signal. It can be provided that the monitoring block stops (inhibits) generator 20 in such a case.

Figure 2:
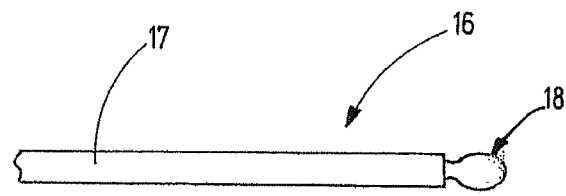

It is further possible to attach sensor 27 at the neutral electrode 19, as schematically illustrated in FIG. 8. Such solutions are particularly suitable for monopolar instruments according to FIG. 2.

However, also the use of bipolar instruments 14' is possible, as schematically illustrated in FIG. 6. Again, the electrode 18 and in addition a neutral electrode 19' is attached to this instrument 14'. In this case both conductors L and N lead from the instrument 14 to generator 20. Apart therefrom the description above applies accordingly in terms of all embodiments that do not specifically refer to the neutral electrode 19 of FIG. 8.

Figure 9:
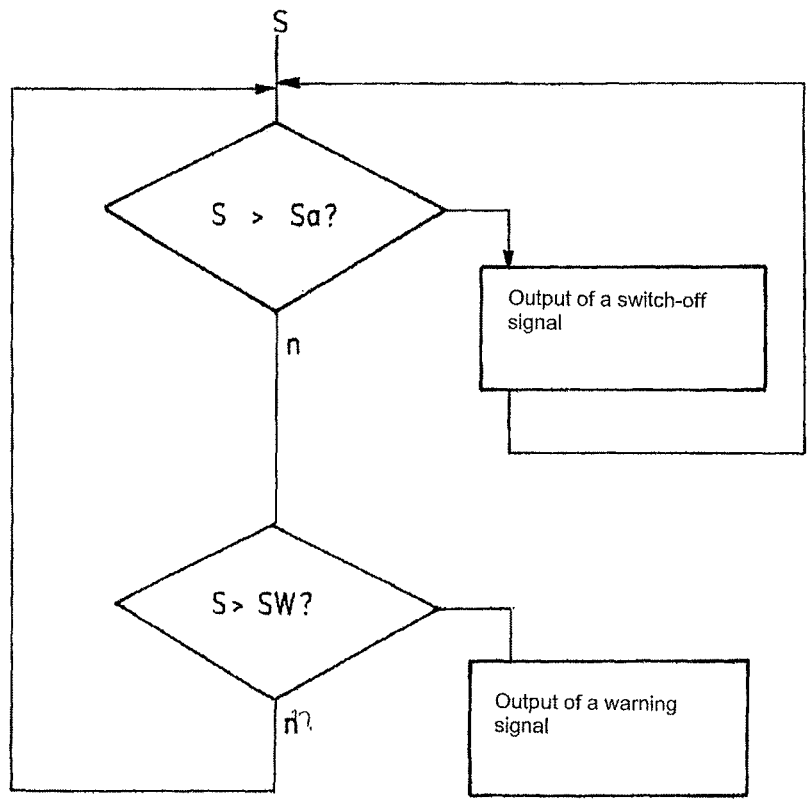
Figure 10:
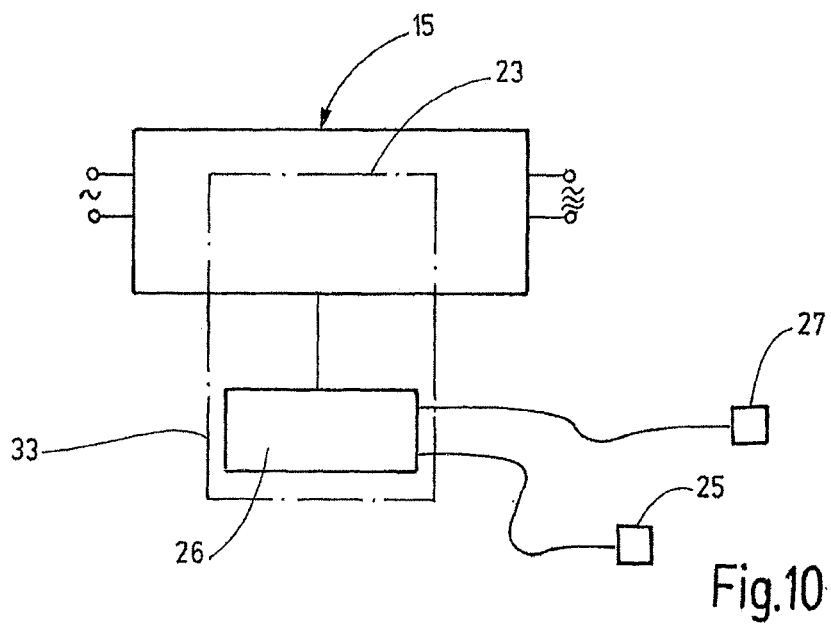

A further modification of embodiments of the invention is a refined monitoring of the sensor signal, e.g. in that it is not only compared with the threshold for deactivation sa, but in addition with a lower threshold (sw), in order to be able to warn the surgeon about the presence of neuromuscular reactions. For this FIG. 9 illustrates the functions of a respective deactivation block. It is configured to first compare signal S with the threshold (sa) for switch-off and if it is reached, to output a switch-off signal. If, however, the threshold (sa) is not reached, the signal S is compared with a lower threshold (sw). If it is not reached no action is undertaken. If, however, signal S exceeds the threshold (sw) a warning signal is output. Such a signal may be an acoustic signal, an optical signal or a tactile signal, e.g. the vibration of a handle. The monitoring of at least two thresholds described just now can be employed in embodiments of the inventive device described above.

In all of the described embodiments it is further possible to carry out only a power reduction of the generator 20 or modification of the modulation type instead of a switch-off of generator 20. However, common to all embodiments of the invention is that at least one sensor 27 is provided that detects a motoric stimulation of the patient, preferably an extremity thereof, and that based on this detected movement the operation of generator 20 and thus the voltage at the electrode 18 of the instrument 14 is influenced. The influencing has particularly the task to mitigate or eliminate the neuromuscular stimulation that is the basis for the movement of the patient.

Embodiments of the inventive surgical device comprise an apparatus 15 with a generator 20, as well as an instrument 14 that is supplied by the generator 20. In addition, a sensor 27 is part of the device that is attached to the patient and particularly to an extremity thereof during operation in order to detect the movement of the patient and particularly the extremity. The sensor is connected with a control device 23 that modifies the operation of generator 20 and particularly switches the generator off, if the sensor detects a movement of the patient 11 exceeding a threshold sa.

Injuries of patient 11 that could occur by involuntary twitches during surgery process are thus avoided.

The invention claimed is:

1. A surgical device for carrying out an electrosurgical intervention on a patient, the surgical device comprising:
   an apparatus that comprises a generator for creation of treatment voltage;
   an instrument that comprises at least one electrode and that is connected to the generator;

at least one sensor attached to the patient configured to detect movement of the patient;

a comparator having first and second blocks, the first block configured to compare an incoming signal (S) from the at least one sensor with at least a first threshold (sw) and the second block configured to a compare the incoming signal (S) with a second threshold (sa), the first threshold (sw) having a lower threshold than the second threshold (sa); and wherein the first block is configured to convey a warning signal if the first threshold (sw) is exceeded and the second block is configured to convey a switch-off signal if the second threshold (sa) is exceeded.

2. The surgical device according to claim 1, further comprising a switch configured to activate and deactivate the generator.

3. The surgical device according to claim 1, wherein the sensor is a movement sensor.

4. The surgical device according to claim 1, wherein the sensor is an acceleration sensor.

5. The surgical device according to claim 1, wherein the sensor includes an adhesive capable of adhering to an extremity of the patient.

6. The surgical device according to claim 1, wherein the sensor includes an attachment band capable of attaching to an extremity of the patient.

7. The surgical device according to claim 6, wherein the switch-off signal comprises a defined signal length duration.

8. The surgical device according to claim 7, wherein the defined signal length is adjustable.

9. The surgical device according to claim 1, wherein the generator is connected with a neutral electrode provided at the instrument.

10. The surgical device according to claim 1, wherein the generator is connected with a neutral electrode that can be attached to the patient.

11. The surgical device according to claim 10, wherein the neutral electrode comprises the sensor.

12. A surgical apparatus comprising:

a generator capable of generating a voltage;

an instrument that comprises at least one electrode and that is connected to the generator;

at least one acceleration sensor attached to the patient capable of detecting movement of the patient;

a comparator having first and second blocks, the first block configured to compare an incoming signal from the at least one sensor with at least a first threshold (sw) and the second block configured to a compare the incoming signal with a second threshold (sa), the first threshold (sw) and the second threshold (sa) different from one another; and wherein the first block is configured to convey a warning signal if the first threshold (sw) is exceeded and the second block is configured to convey a switch-off signal if the second threshold (sa) is exceeded.

13. The surgical apparatus according to claim 12, wherein the instrument further comprises a handle capable of vibrating in response to the warning signal.

* * * * *